(12) United States Patent
Kawashima et al.

(10) Patent No.: US 11,162,828 B2
(45) Date of Patent: Nov. 2, 2021

(54) SENSOR PROBE HAVING A CIRCUIT HOUSING FIXABLE AT A PLURALITY OF ROTATION POSITIONS

(71) Applicant: Yokogawa Electric Corporation, Tokyo (JP)

(72) Inventors: Takuya Kawashima, Musashino (JP); Toshiki Miyasaka, Musashino (JP); Junichi Matsuo, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 271 days.

(21) Appl. No.: 16/394,777

(22) Filed: Apr. 25, 2019

(65) Prior Publication Data
US 2019/0331511 A1    Oct. 31, 2019

(30) Foreign Application Priority Data

Apr. 26, 2018 (JP) .............................. JP2018-085572

(51) Int. Cl.
*G01F 1/66* (2006.01)
*G01F 1/32* (2006.01)
*G01F 1/86* (2006.01)

(52) U.S. Cl.
CPC ............ *G01F 1/661* (2013.01); *G01F 1/3209* (2013.01); *G01F 1/329* (2013.01); *G01F 1/662* (2013.01); *G01F 1/86* (2013.01)

(58) Field of Classification Search
None
See application file for complete search history.

(56) References Cited

U.S. PATENT DOCUMENTS

| 6,584,860 B1* | 7/2003 | Feller ...................... G01F 1/106 73/861.25 |
| 9,341,522 B2* | 5/2016 | Kitzman ................... G01K 1/08 |
| 10,082,416 B1* | 9/2018 | Lease ..................... F17C 13/028 |
| 2009/0122831 A1* | 5/2009 | Chen ....................... G01F 15/14 374/142 |
| 2014/0183380 A1 | 7/2014 | Ukon et al. |

FOREIGN PATENT DOCUMENTS

| JP | 7-151628 A | 6/1995 |
| JP | 2012-037419 A | 2/2012 |
| JP | 2012-058096 A | 3/2012 |
| JP | 2012-112854 A | 6/2012 |
| WO | 2007090421 A1 | 8/2007 |
| WO | 2012/062595 A1 | 5/2012 |

* cited by examiner

*Primary Examiner* — Andre J Allen
*Assistant Examiner* — Jermaine L Jenkins
(74) *Attorney, Agent, or Firm* — Sughrue Mion, PLLC

(57) ABSTRACT

A measurement apparatus includes a sensor probe and a circuit housing. The sensor probe is insertable through an opening provided in a flow path wall of a flow path through which a fluid to be measured flows and is used in a predetermined orientation relative to the flow direction of the fluid to be measured. The circuit housing includes a display, disposed outside of the flow path, and connects to the sensor probe. The circuit housing is fixable at a plurality of rotation positions relative to the sensor probe about an axis along the insertion direction of the sensor probe. The measurement apparatus allows the display direction of the display to be selected regardless of the orientation of the sensor probe.

11 Claims, 9 Drawing Sheets

SENSOR PROBE HAVING A CIRCUIT HOUSING FIXABLE AT A PLURALITY OF ROTATION POSITIONS

CROSS-REFERENCE TO RELATED APPLICATION

The present application claims priority to and the benefit of Japanese Patent Application No. 2018-85572 filed Apr. 26, 2018, the entire contents of which are incorporated herein by reference.

TECHNICAL FIELD

The present disclosure relates to a measurement apparatus.

BACKGROUND

A known measurement apparatus includes a sensor probe and a circuit housing that includes a display. A portion of the sensor probe is disposed in a flow path of a fluid to be measured. The measurement apparatus displays information, measured by the sensor probe, related to the fluid to be measured on the display, which is disposed outside of the flow path.

For example, patent literature (PTL) 1 discloses a field device, as a measurement apparatus, capable of rotating a display device, serving as the display, about an axis along the display direction. PTL 2 discloses a field device, as a measurement apparatus, that rotates and outputs the display content of a display device, serving as the display, on the basis of the inclination of the field device upon installment.

CITATION LIST

Patent Literature

PTL 1: JP201258096A
PTL 2: JP201237419A

SUMMARY

A measurement apparatus according to an embodiment includes a sensor probe and a circuit housing. The sensor probe is insertable through an opening provided in a flow path wall of a flow path through which a fluid to be measured flows and is used in a predetermined orientation relative to the flow direction of the fluid to be measured. The circuit housing includes a display and connects to the sensor probe, the display being disposed outside of the flow path. The circuit housing is fixable at a plurality of rotation positions relative to the sensor probe about an axis along the insertion direction of the sensor probe.

BRIEF DESCRIPTION OF THE DRAWINGS

In the accompanying drawings.

DETAILED DESCRIPTION

Figure 1:
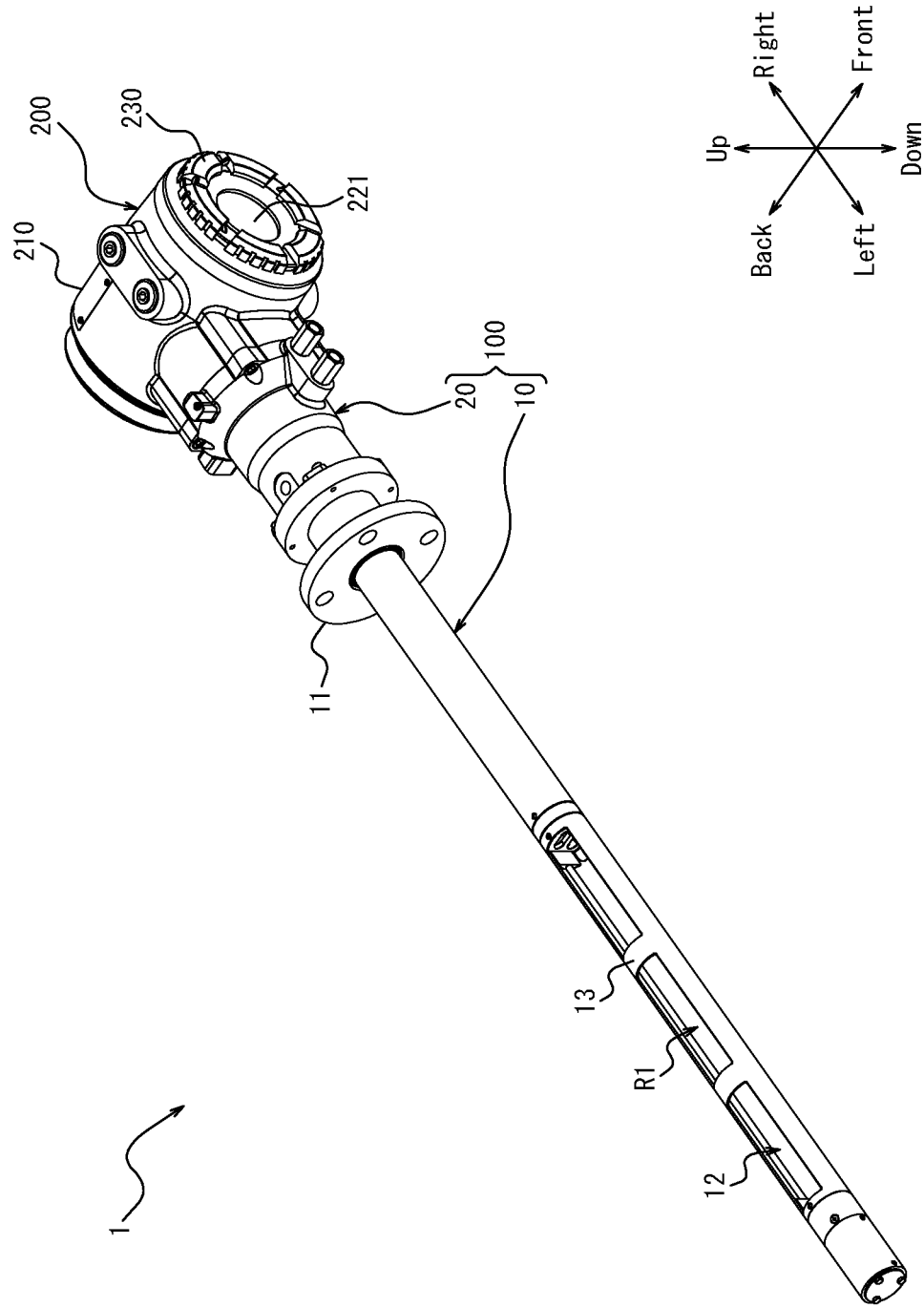
FIG. 1 is a perspective view, from above, of a measurement apparatus according to an embodiment of the present disclosure.

The measurement apparatuses disclosed in PTL 1 and PTL 2 can rotate the display content about an axis along the display direction. The measurement apparatus sometimes needs to be used with the sensor probe in a predetermined orientation relative to the flow direction of the fluid to be measured. In this case, the display direction of the display in the measurement apparatus disclosed in PTL 1 or PTL 2 might face a direction other than the direction desired by the user, since the display direction of the display changes in conjunction with the orientation of the sensor probe.

It is an objective of the present disclosure to provide a measurement apparatus allowing the display direction of the display to be selected regardless of the orientation of the sensor probe.

A measurement apparatus according to an embodiment includes a sensor probe and a circuit housing. The sensor probe is insertable through an opening provided in a flow path wall of a flow path through which a fluid to be measured flows and is used in a predetermined orientation relative to the flow direction of the fluid to be measured. The circuit housing includes a display and connects to the sensor probe, the display being disposed outside of the flow path. The circuit housing is fixable at a plurality of rotation positions relative to the sensor probe about an axis along the insertion direction of the sensor probe. This configuration allows the display direction of the display to be selected regardless of the orientation of the sensor probe.

In a measurement apparatus according to an embodiment, the sensor probe may include a first connecting portion, and the circuit housing may include a second connecting portion that connects to the first connecting portion. One of the first connecting portion and the second connecting portion may include a plurality of first connecting elements arranged about the axis along the insertion direction, and the other one of the first connecting portion and the second connecting portion may include one or more second connecting elements connectable to the plurality of first connecting elements at the plurality of rotation positions. This configuration allows the sensor probe and the circuit housing to be connected by a simple structure.

In a measurement apparatus according to an embodiment, the display may be fixable at a plurality of rotation positions relative to the sensor probe about an axis along a display direction. This configuration allows the angle at which content is displayed by the display to be selected regardless of the orientation of the sensor probe.

In a measurement apparatus according to an embodiment, the circuit housing may include a casing and a circuit portion that includes the display. The circuit portion may include a third connecting portion. The casing may include a fourth connecting portion. One of the third connecting portion and the fourth connecting portion may include a plurality of third connecting elements arranged about the axis along the display direction, and the other one of the third connecting portion and the fourth connecting portion may include one or more fourth connecting elements connectable to the plurality of third connecting elements at the plurality of rotation positions where the display is fixable relative to the sensor probe about the axis along the display direction. This configuration allows the angle at which content is displayed by the display to be selectable with a simple structure.

In a measurement apparatus according to an embodiment, the circuit housing may include a circuit portion that includes the display. The display may include a third connecting portion. A portion of the circuit portion other than the display may include a fourth connecting portion. One of the third connecting portion and the fourth connecting portion may include a plurality of third connecting elements arranged about the axis along the display direction, and the other one of the third connecting portion and the fourth connecting portion may include one or more fourth connecting elements connectable to the plurality of third connecting elements at the plurality of rotation positions where the display is fixable relative to the sensor probe about the axis along the display direction. This configuration allows the angle at which content is displayed by the display to be selectable with a simple structure.

In a measurement apparatus according to an embodiment, the plurality of rotation positions of the circuit housing relative to the sensor probe may include four rotation positions differing by substantially 90°. This configuration makes it easier to orient the display direction of the display in the direction desired by the user.

In a measurement apparatus according to an embodiment, the plurality of rotation positions of the display relative to the sensor probe may include four rotation positions differing by substantially 90°. This configuration makes it easier to set the angle at which content is displayed by the display to the angle desired by the user.

In a measurement apparatus according to an embodiment, the insertion direction may be a direction substantially orthogonal to an extending direction of the flow path, and the display direction may be a direction substantially orthogonal to the insertion direction. This configuration makes it even easier to orient the display direction of the display in the direction desired by the user.

In a measurement apparatus according to an embodiment, the sensor probe may include an attachment portion attachable to an outer surface of the flow path wall. The attachment portion may be positioned towards the flow path from a connection position between the sensor probe and the circuit housing. This configuration allows the rotation position of the circuit housing relative to the sensor probe about the connection axis to be changed even after the sensor probe is installed in the flow path.

In a measuring apparatus according to an embodiment, each of the plurality of first connecting elements and the one or more second connecting elements may be a connector configured to mechanically and electrically connect the sensor probe and the circuit housing to each other. This configuration allows the sensor probe and the circuit housing to be connected mechanically and electrically by a simple structure.

In a measuring apparatus according to an embodiment, the connector may be a floating connector. This configuration can easily absorb misalignment between connectors that are connected.

In a measurement apparatus according to an embodiment, the sensor probe may include an optical emitter configured to irradiate measurement light into a measurement region including the fluid to be measured, a probe extending along an optical axis of the measurement light so as to overlap the measurement region, a reflector positioned at an opposite tip of the probe from the optical emitter and configured to reflect the measurement light, and an optical receiver configured to receive the measurement light reflected by the reflector. This configuration can achieve the aforementioned effect of allowing selection of the display direction of the display regardless of the orientation of the sensor probe in a measurement apparatus that includes a sensor probe capable of measuring a fluid with light.

The present disclosure can provide a measurement apparatus allowing the display direction of the display to be selected regardless of the orientation of the sensor probe.

Embodiments of this disclosure are described below, with reference to the drawings. The front-back, left-right, and up-down directions referred to below are based on the directions of the arrows in the drawings. The directions of the arrows are consistent in FIGS. 1 through 4 and FIGS. 9 through 11.

Figure 2:
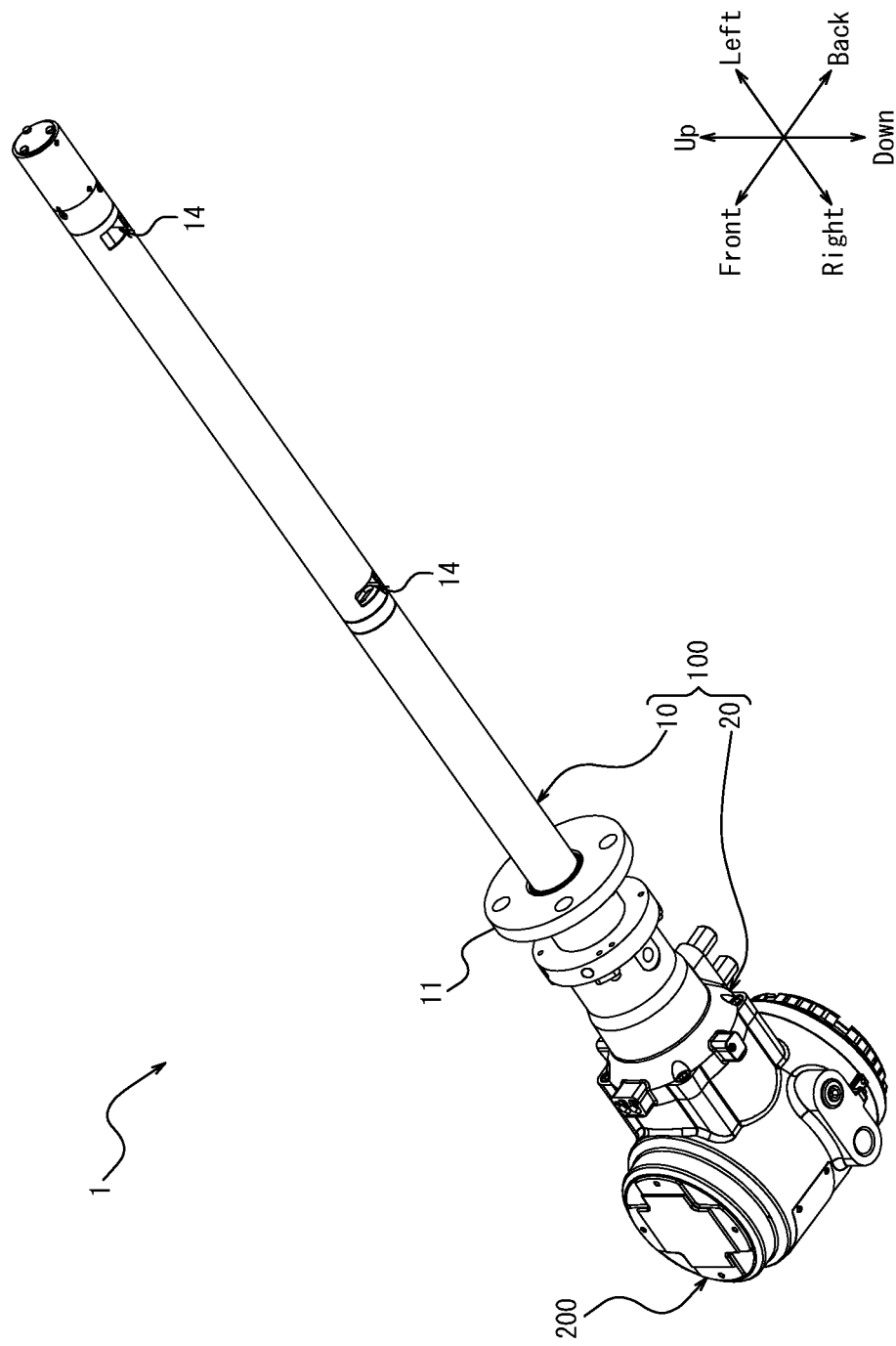
FIG. 2 is a perspective view, from below, of the measurement apparatus of FIG. 1.
Figure 3:
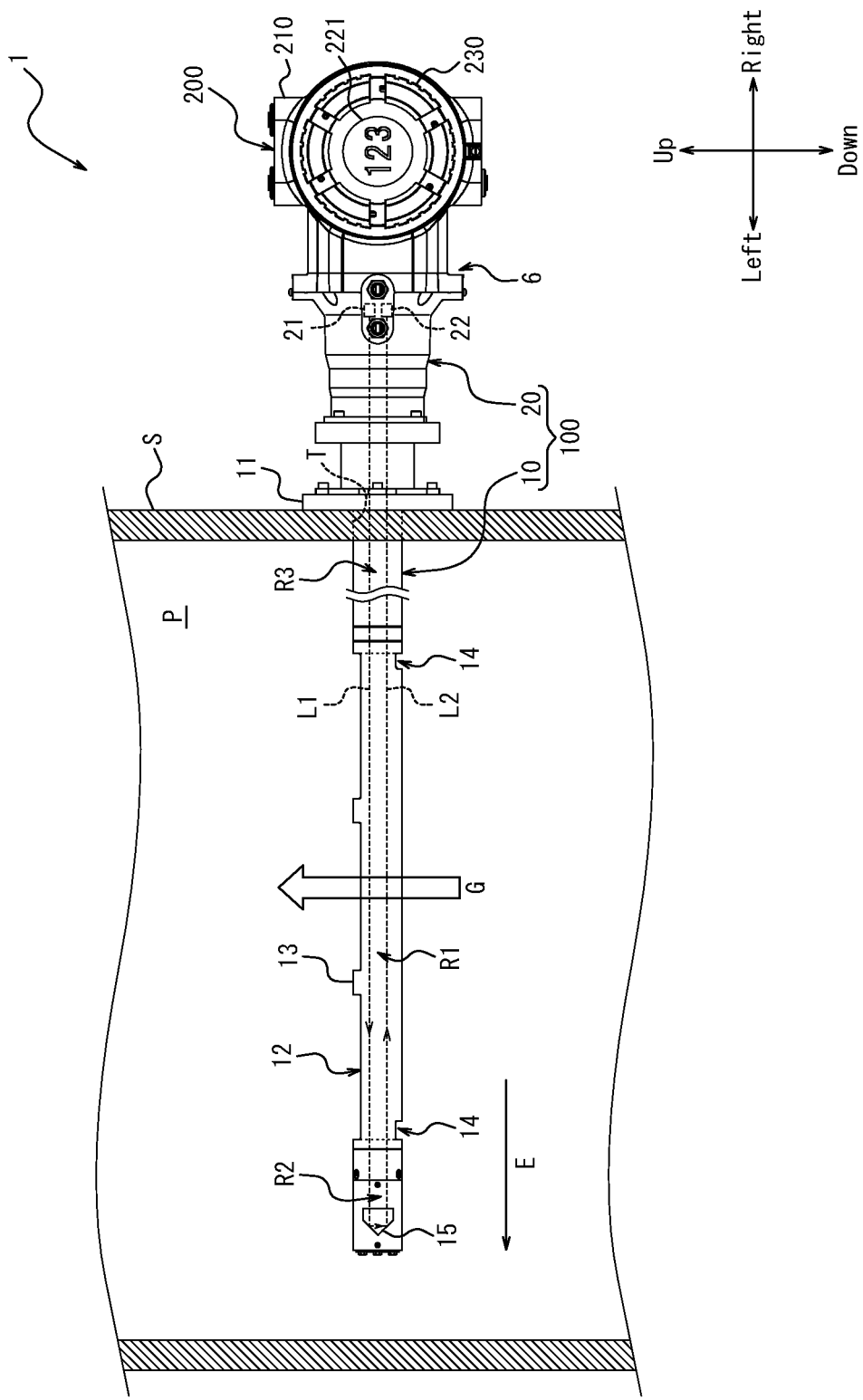
FIG. 3 is a front view illustrating a first usage state of the measurement apparatus of FIG. 1.
Figure 4:
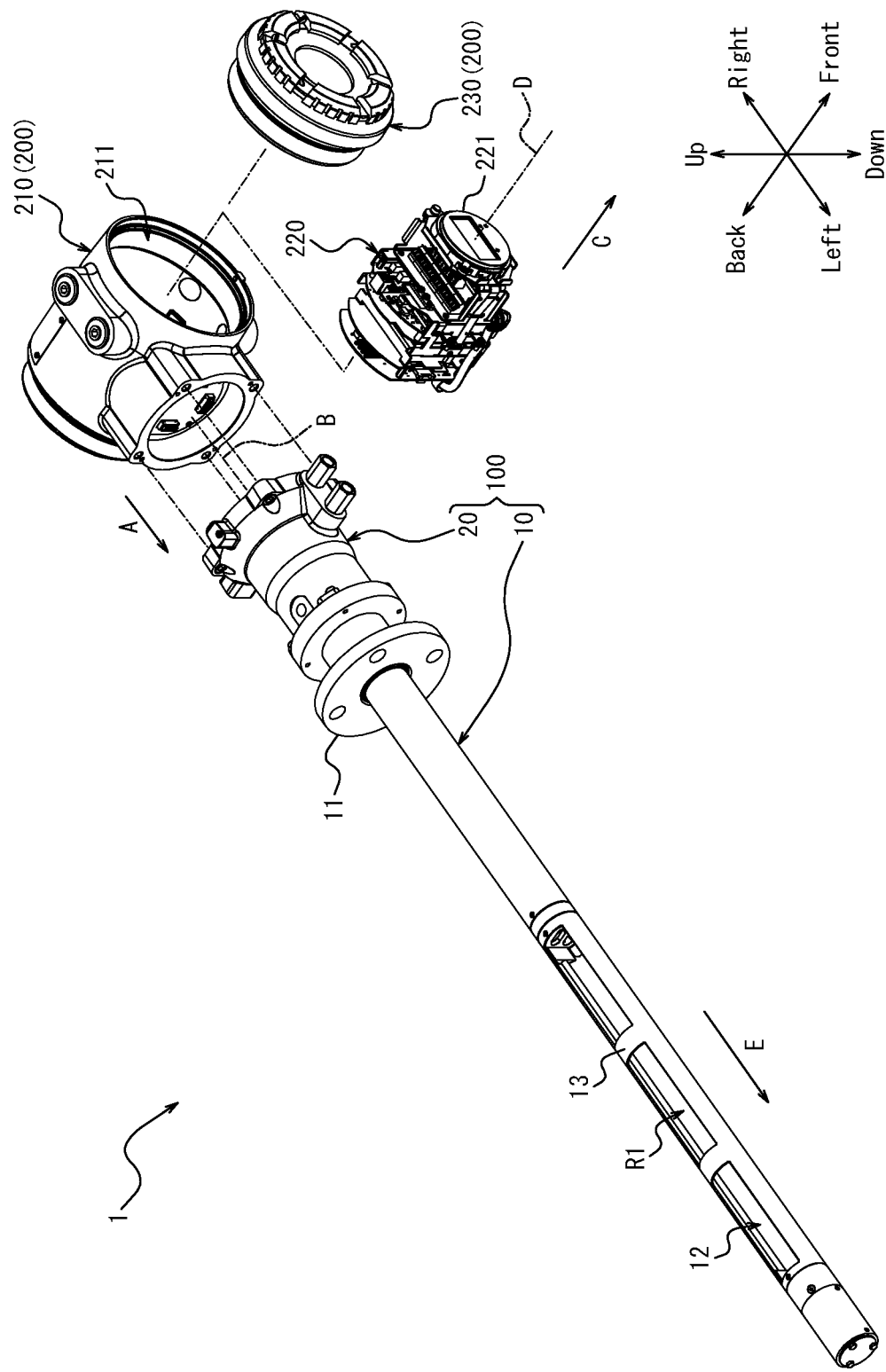
FIG. 4 is an exploded perspective view, from above, illustrating the measurement apparatus of FIG. 1.

FIG. 1 is a perspective view, from above, of a gas analyzer 1 as a measurement apparatus according to an embodiment of the present disclosure. FIG. 2 is a perspective view, from below, of the gas analyzer 1. FIG. 3 is a front view illustrating a first usage state of the gas analyzer 1. In the example in FIG. 3, the gas analyzer 1 is attached to a flow path wall S to measure a predetermined physical quantity of a gas to be measured G, which is a fluid to be measured flowing through a flow path P. The flow path P may, for example, be piping, a flue, a combustion furnace, or the like. The predetermined physical quantity of the gas to be measured G includes the component concentration of a target component, for example. FIG. 4 is an exploded perspective view, from above, of the gas analyzer 1.

The functions and configuration of the gas analyzer 1 as a measurement apparatus according to an embodiment are now described with reference to FIGS. 1 to 4.

As illustrated in FIG. 3, the gas analyzer 1 is attached directly to the flow path wall S of the flow path P through which the gas to be measured G flows. The gas to be measured G includes a process gas, for example. The gas analyzer 1 analyzes the component concentration of a measurement target component. The gas to be measured G may, for example, include a gas such as CO, $CO_2$, $H_2O$, $C_nH_m$ (a hydrocarbon), $NH_3$, or $O_2$.

The gas analyzer 1 includes a probe-type tunable diode laser absorption spectroscopy (TDLAS) gas analyzer, for example, that has an explosion-proof structure and is used in an explosion-proof area. Probe-type refers, for example, to how the gas analyzer 1 has a light source, a reflecting structure, and a photodetector integrally built therein and is structured for insertion from one end into the flow path P through which the gas to be measured G flows. The gas analyzer 1 analyzes the component concentration of the measurement target component by irradiating a laser beam that becomes measurement light onto the gas to be measured G.

The gas molecules included in the gas to be measured G exhibit a light absorption spectrum based on the vibration and rotational energy transition of the molecules in a region from infrared to near infrared. The absorption spectrum is unique to the component molecules. By the Lambert-Beer law, the absorbance of gas molecules with regard to the measurement light is proportional to their component concentration and the optical path length. Accordingly, the component concentration of the measurement target component can be analyzed by measuring the absorption spectrum intensity.

In TDLAS, a semiconductor laser beam with a sufficiently narrower line width than the absorption line width of the energy transition of the gas molecules is irradiated onto the gas to be measured G as measurement light. The wavelength of measurement light is swept by high-speed modulation of the drive current for the semiconductor laser. The optical intensity of the measurement light that passes through the gas to be measured G is measured to acquire one independent absorption spectrum.

The sweep range of the laser beam differs depending on use. When the measurement target component is $O_2$, the line width of the laser beam is, for example, 0.0002 nm, and the sweep width is, for example, 0.1 nm to 0.2 nm. The absorption spectrum is measured by sweeping over a sweep width of 0.1 nm to 0.2 nm. The component concentration of the measurement target component is calculated by performing concentration conversion on the acquired single absorption spectrum. Methods of concentration conversion include known methods, such as the peak height method, the spectral area method, and the 2f method.

As illustrated in FIGS. 1 and 2, the gas analyzer 1 includes a sensor probe 100 and a circuit housing 200. The circuit housing 200 is used by being connected to the sensor probe 100, as illustrated in FIGS. 1 to 3. The circuit housing 200 can be fixed at a plurality of rotation positions relative to the sensor probe 100 about an axis (connection axis B) along a connection direction A of connection to the sensor probe 100, as illustrated in FIG. 4. Details are provided below. In the present embodiment, a display 221 included in the circuit housing 200 can be fixed at a plurality of rotation positions relative to the sensor probe 100 about an axis (display axis D) along a display direction C, as illustrated in FIG. 4. Details are provided below. The state in which the rotation position of each constituent element of the gas analyzer 1 is as illustrated in FIGS. 1 to 3 is designated as a first rotation state.

The sensor probe 100 outputs a signal corresponding to a predetermined physical property value of the fluid to be measured to the circuit housing 200. As illustrated in FIG. 3, at least a portion of the sensor probe 100 is insertable through an opening T provided in the flow path wall S of the flow path P through which the gas to be measured G, which serves as the fluid to be measured, flows. The sensor probe 100 is used in a predetermined orientation relative to the flow direction of the gas to be measured G. FIG. 3 illustrates an insertion direction E of the sensor probe 100 into the flow path P. In FIG. 3, the flow direction of the gas to be measured G is indicated by a white arrow with a black outline. As illustrated in FIG. 4, the insertion direction E of the sensor probe 100 into the flow path P is substantially the same direction as the connection direction A of the circuit housing 200 to the sensor probe 100. Accordingly, the connection axis B is both an axis along the connection direction A and an axis along the insertion direction E, as illustrated in FIG. 4.

The sensor probe 100 of the present embodiment includes a probe 10 and a sensor 20, as illustrated in FIGS. 1 and 2. The probe 10 is a cylindrical body with a substantially circular cross-sectional shape, for example. The probe 10 is formed by any metal member.

As illustrated in FIG. 1, the probe 10 in the first rotation state extends in the left-right direction and includes an opening 12 facing upward. The probe 10 includes a plurality of ribs 13 provided in the opening 12 to maintain the strength of the probe 10. As illustrated in FIG. 2, the probe 10 in the first rotation state includes notches 14 formed by cutting out a portion of the surface of the probe 10 from below, towards the inside. The notches 14 are respectively formed at substantially the same left-right positions as the left-right ends of the opening 12. The length of the probe 10 in the extending direction is, for example, approximately 0.5 m to 2 m.

As illustrated in FIG. 3, the probe 10 includes a reflector 15 in the inner section at the tip. The reflector 15 includes any reflecting structure for reflecting the measurement light, such as a corner cube prism or a retroreflector. The reflector 15 reflects measurement light from the optical emitter 21, described below.

The sensor 20 is fixed at the opposite end from the tip of the probe 10 where the reflector 15 is attached. As illustrated in FIG. 3, the sensor 20 includes the optical emitter 21 for irradiating the measurement light onto the gas to be measured G and an optical receiver 22 for receiving the measurement light reflected by the reflector 15. The casing of the sensor 20 is, for example, an explosion-proof container that stores the optical emitter 21 and the optical receiver 22.

The optical emitter 21 includes any light source capable of measuring the gas to be measured G by TDLAS. For example, the optical emitter 21 includes a semiconductor laser. The optical receiver 22 includes any photodetector capable of measuring the gas to be measured G by TDLAS. For example, the optical receiver 22 includes a photodiode.

As illustrated in FIG. 3, the probe 10 is supported with the majority of the probe 10 inside the flow path P. The sensor 20 is supported while outside of the flow path P, as illustrated in FIG. 3. Specifically, the gas analyzer 1 includes an attachment portion 11, such as a flange, formed as a portion of the probe 10. The gas analyzer 1 is supported by the flow path wall S by virtue of the attachment portion 11 being attached to the outer wall of the flow path wall S. At this time, the opening 12 exposes the corresponding interior section of the probe 10 inside the flow path P. The notches 14 connect the inner section of the probe 10, exposed in the flow path P by the opening 12, with the space in the flow path P below the inner section.

In the example in FIG. 3, the flow path P extends in the up-down direction, and the flow direction of the gas to be measured G is the direction from bottom to top. With respect to this flow direction of the gas to be measured G, the probe 10 is required to be used with the notches 14 facing downward, i.e. upstream in the flow direction, and the opening 12 facing upward, i.e. downstream in the flow direction, as illustrated in FIG. 3. When the probe 10 is used while having the aforementioned orientation relative to the flow direction of the gas to be measured G, a measurement region R1 can be filled with the gas to be measured G, while regions R2 and R3 can be filled with a purge gas, as described below.

In the present embodiment, the insertion direction E of the sensor probe 100 into the flow path P is substantially orthogonal to the flow direction of the gas to be measured G, as illustrated in FIG. 3. The probe 10 of the present embodiment extends in a substantially orthogonal direction to the flow direction of the gas to be measured G inside the flow path P. Therefore, a portion of the gas to be measured G flowing in the flow path P flows into the measurement region R1 inside the probe 10 from below through the notches 14. Another portion of the gas to be measured G wraps around and flows into the measurement region R1 inside the probe 10 through the opening 12 from above. In this way, the gas to be measured G flowing through the flow path P flows inside the probe 10. The gas to be measured G that flowed inside the probe 10 flows out into the flow path P once again through the opening 12, for example. Here, the measurement region R1 includes an interior space of the probe 10 exposed to the flow path P by the opening 12. In this way, the measurement region R1 is filled with the gas to be measured G.

On the other hand, a purge gas is supplied by any appropriate mechanism to the regions R2 and R3 formed on the left and right sides of the measurement region R1 inside the probe 10. In FIG. 3, the boundary between the measurement region R1 and the region R2 and the boundary between the measurement region R1 and the region R3 are indicated by dotted lines. The purge gas suppresses contact between the gas to be measured G and optical components such as the reflector 15, the optical emitter 21, and the optical receiver 22 to prevent problems, such as contamination or corrosion, of these optical components. The regions R2 and R3 are thus filled with the purge gas.

The notches 14 suppress mixing of the gas to be measured G and the purge gas between the measurement region R1 and the regions R2 and R3. Specifically, the notches 14 guide the gas to be measured G from the flow path P into the measurement region R1 in the probe 10, thereby suppressing mixing of the purge gas into the measurement region R1. Similarly, the notches 14 suppress mixing of the gas to be measured G into the regions R2 and R3.

The optical emitter 21 irradiates measurement light towards the reflector 15 of the probe 10. In FIG. 3, the portion of the measurement light before being reflected by the reflector 15 is indicated as emitted light L1. The optical emitter 21 irradiates the emitted light L1 into the measurement region R1 that includes the gas to be measured G. The emitted light L1 propagates inside the probe 10, which extends along the optical axis of the emitted light L1 so as to overlap the measurement region R1. The emitted light L1 is then incident on the reflector 15. The reflector 15 is positioned at the tip of the probe 10 at the opposite end from the optical emitter 21 and reflects the emitted light L1 that passed through the measurement region R1. In FIG. 3, the measurement light after being reflected by the reflector 15 is indicated as reflected light L2. The reflected light L2 again passes through the inside of the probe 10 that includes the measurement region R1. The optical receiver 22 receives the reflected light L2 that was reflected by the reflector 15 and passed through the measurement region R1.

The optical receiver 22 electrically amplifies a measurement signal related to the detected measurement light using any appropriate amplifier circuit and then outputs the detected optical intensity of the measurement light as a scan signal to a circuit portion 220 of the circuit housing 200, described below. A portion of each of the emitted light L1 and the reflected light L2 is absorbed, when passing through the inside of the probe 10, by the gas to be measured G flowing in the measurement region R1. The component concentration of the measurement target component in the gas to be measured G is calculated by measuring the absorption spectrum on the basis of the measurement signal acquired by the optical receiver 22.

In the above-described probe-type gas analyzer 1, each of the optical emitter 21, the reflector 15, and the optical receiver 22 satisfies predetermined conditions in a state of attachment at the installation site. The predetermined conditions include positional relationships between these optical components such that the emitted light L1 irradiated from the optical emitter 21 passes through the measurement region R1 and is reflected by the reflector 15, and the reflected light L2 passes back through the measurement region R1 and is incident on the optical receiver 22. In some cases, the reflector 15 may not be arranged symmetrically in the circumferential direction of the probe 10. The positional relationships in the circumferential direction between the probe 10 and the sensor 20 are therefore fixed in the sensor probe 100.

The circuit housing 200 of the present embodiment includes a casing 210, a circuit portion 220 including a display 221, and a lid 230. The circuit housing 200 converts a signal input from the sensor probe 100 into a physical property value using the circuit portion 220 and causes the display 221 to display information of the physical property value. The casing 210 defines an opening 211 and can house the circuit portion 220 inside the casing 210 through the opening 211. The lid 230 is attachable to the casing 210 so as to cover the opening 211. The casing 210 and the lid 230 isolate the circuit portion 220 housed inside the casing 210 from the outside. The casing 210 and the lid 230 together form an explosion-proof container, for example.

The casing 210 connects to the sensor probe 100. The casing 210 electrically connects the sensor 20 of the sensor probe 100 with the circuit portion 220. The circuit portion 220 has a calculation unit including one or more processors, for example. The calculation unit controls overall operations of the gas analyzer 1, including the optical emitter 21 and the optical receiver 22.

The display 221 is disposed outside of the flow path P. In the present embodiment, the attachment portion 11 is positioned towards the flow path P from a connection position 6 between the sensor probe 100 and the circuit housing 200, as illustrated in FIG. 3. Accordingly, the entire circuit housing 200 including the display 221 is disposed outside of the flow path P. In other words, the circuit housing 200 is connected to the sensor probe 100 outside of the flow path P. The display 221 is capable of displaying information and the like of the predetermined physical property value of the gas to be measured G, such as the component concentration of the target component included in the gas to be measured G, as measured by the sensor probe 100. The display 221 includes a liquid crystal display device, for example. The display direction C of the display 221 is a direction not parallel to either the connection direction A of the circuit housing 200 to the sensor probe 100 or the insertion direction E of the sensor probe 100 into the flow path P. In the present embodiment, the display direction C of the display 221 is a direction substantially orthogonal to the connection direction A and the insertion direction E of the sensor probe 100 into the flow path P, as illustrated in FIG. 4. The display direction C of the display 221 in the example in FIG. 3 is a direction facing out of the page. The display content is displayed in the left-right direction for better visibility for a user standing upright, so that the angle of the content displayed by the display 221 is set to the angle desired by the user.

As illustrated in FIG. 3, the lid 230 includes a member allowing the display content of the display 221 to be seen from the outside when the lid 230 is attached to the casing 210 to cover the opening 211.

Figure 5:
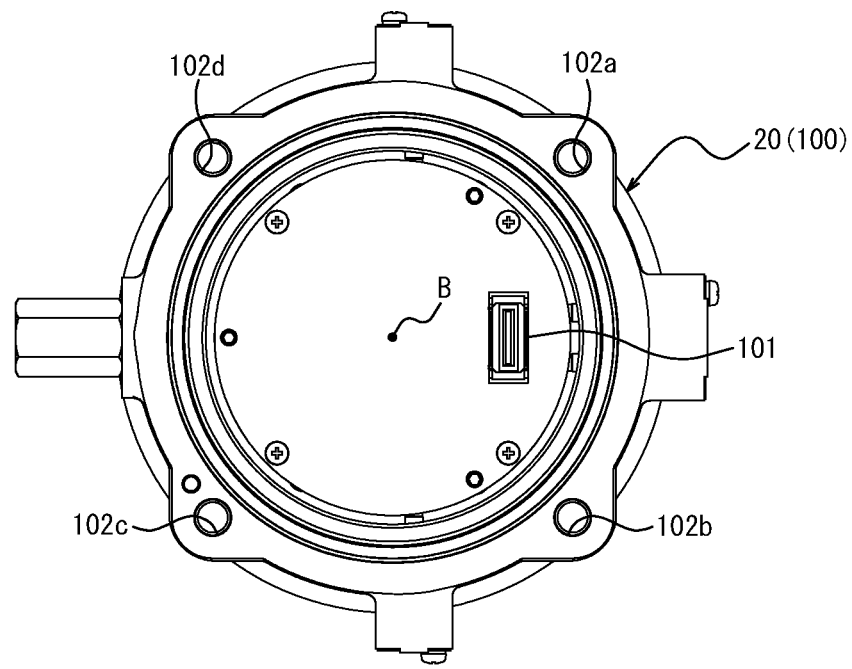
FIG. 5 illustrates an example of a first connecting portion of a sensor probe.
Figure 6:
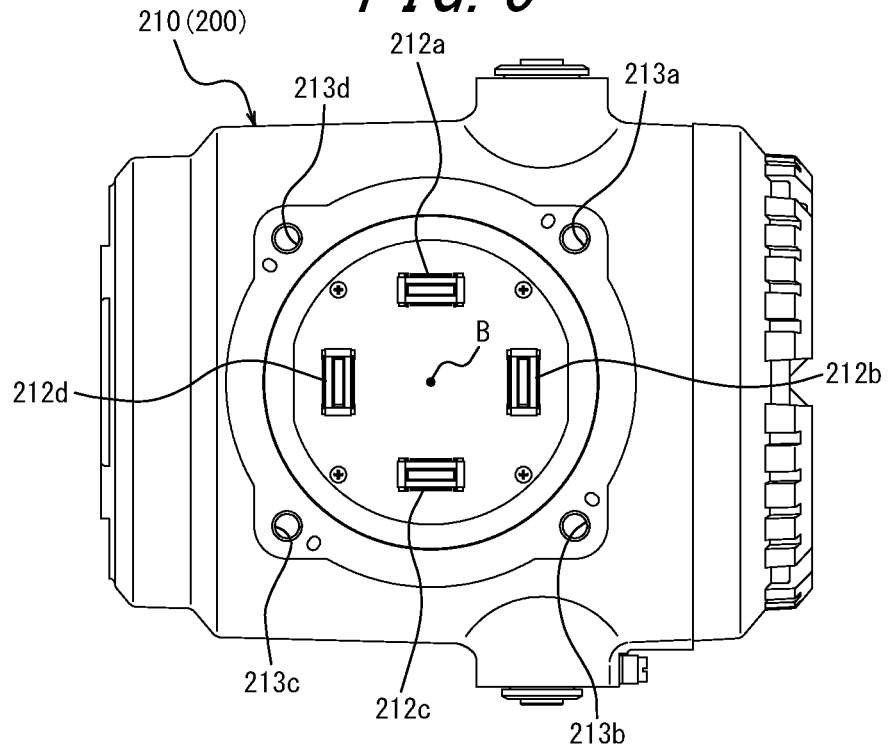
FIG. 6 illustrates an example of a second connecting portion of a circuit housing.

The form of connection between the sensor probe 100 and the circuit housing 200 is described below with reference to FIGS. 5 and 6. The sensor probe 100 includes a first connecting portion, details of which are provided below. The circuit housing 200 includes a second connecting portion that connects to the first connecting portion. One of the first connecting portion and the second connecting portion includes a plurality of first connecting elements arranged about the connection axis B. The other one of the first connecting portion and the second connecting portion includes one or more second connecting elements connectable to the first connecting elements at a plurality of rotation positions where the circuit housing 200 is fixable relative to the sensor probe 100 about the connection axis B. FIG. 5 illustrates an example of the first connecting portion of the sensor probe 100. FIG. 6 illustrates an example of the second connecting portion of the circuit housing 200. The sensor probe 100 and the circuit housing 200 connect to each other mechanically and electrically via the first connecting portion of the sensor probe 100 and the second connecting portion of the circuit housing 200.

In the example in FIG. 5, the sensor 20 of the sensor probe 100 includes one first connector 101 and four first holes 102a to 102d as the first connecting portion. In the example in FIG. 6, the casing 210 of the circuit housing 200 includes four second connectors 212a to 212d and four second holes 213a to 213d as the second connecting portion. The first connecting portion includes the one first connector 101 as the above-described one or more second connecting elements. The second connector includes the four second connectors 212a to 212d as the above-described plurality of first connecting elements. The four second connectors 212a to 212d are disposed about the connection axis B, as illustrated in FIG. 6, and the first connector 101 is connectable to the four second connectors 212a to 212d at a plurality of rotation positions where the circuit housing 200 is fixable relative to the sensor probe 100.

The sensor 20 and the circuit portion 220 are electrically connected when the first connector 101 is connected to one of the four second connectors 212a to 212d. As illustrated in FIG. 5, the first connector 101 is disposed at a position located a predetermined distance from the connection axis B at the right end of the sensor probe 100 (see FIG. 4). As illustrated in FIG. 6, the four second connectors 212a to 212d are connected at positions at the left end of the circuit housing 200 (see FIG. 4) at the predetermined distance from the connection axis B, i.e. at a distance equivalent to the distance of the first connector 101 from the connection axis B. The positions are at substantially equal intervals of substantially 90° from each other around a circle centered on the connection axis B. Accordingly, the sensor probe 100 and the circuit housing 200 can be connected via the first connector 101 and one of the four second connectors 212a to 212d at positions substantially 90° apart from one another around the connection axis B. In other words, the rotation positions that the circuit housing 200 can adopt when connecting to the sensor probe 100 include four rotation positions differing by substantially 90°.

Floating connectors comprising a floating structure, for example, may be used as the first connector 101 or the four second connectors 212a to 212d. The use of floating connectors allows movement in at least one of the connection direction A and a direction orthogonal to the connection direction A and can absorb misalignment between connectors that are connected.

When the first connector 101 is connected to any of the four second connectors 212a to 212d, the four first holes 102a to 102d are at positions corresponding to the four second holes 213a to 213d. In this state, screws or the like can be attached so as to pass through the four first holes 102a to 102d and the four second holes 213a to 213d, thereby reinforcing the physical connection between the sensor probe 100 and the circuit housing 200.

FIGS. 5 and 6 illustrate the one first connector 101 as the first connecting portion and the four second connectors 212a to 212d as the second connecting portion. In the case of one first connector, however, it suffices to provide any plural number of second connectors, such as two, three, or five or more. In this case, each of the plurality of second connectors is disposed at the above described predetermined distance from the connection axis B at the left end of the circuit housing 200 (see FIG. 4), in the same way as above. Consequently, the number of rotation positions that the circuit housing 200 can adopt when connecting to the sensor probe 100 is not limited to four and may instead be two, three, or five or more. Two or three of rotation positions, for example, would be of substantially 90° from each other around the connection axis B. Two, three or five or more of rotation positions, for example, would be substantially equal intervals around the connection axis B.

The relationship between the first connector and the second connectors in terms of number and arrangement may be reversed. Specifically, a plurality of first connectors and one second connector may be provided. Furthermore, instead of or in addition to the first and second connectors that mechanically and electrically connect the sensor probe 100 and the circuit housing 200, a cable for electrically connecting the sensor 20 and the circuit portion 220 may be used. Use of the first and second connectors, however, facilitates attachment and detachment and is therefore more preferable than use of a cable. The first and second connectors may be configured to provide no mechanical connection but non-contact electrical connection.

Figure 7:
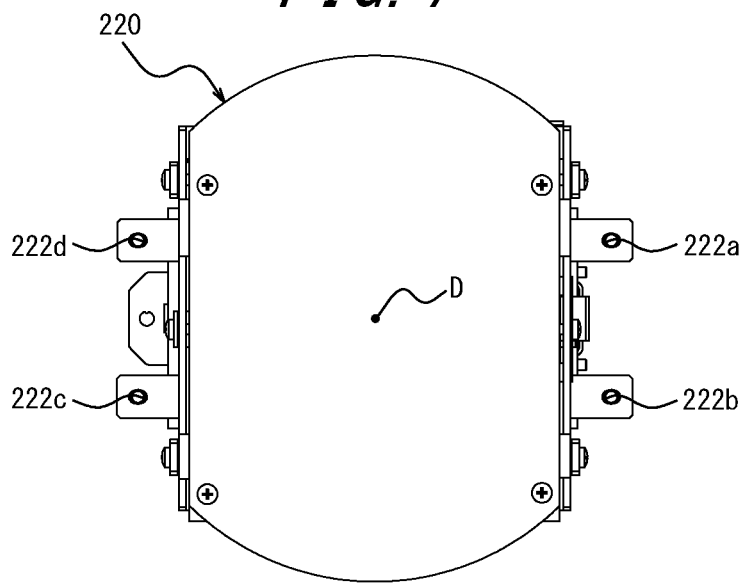
FIG. 7 illustrates an example of a third connecting portion of a circuit portion.
Figure 8:
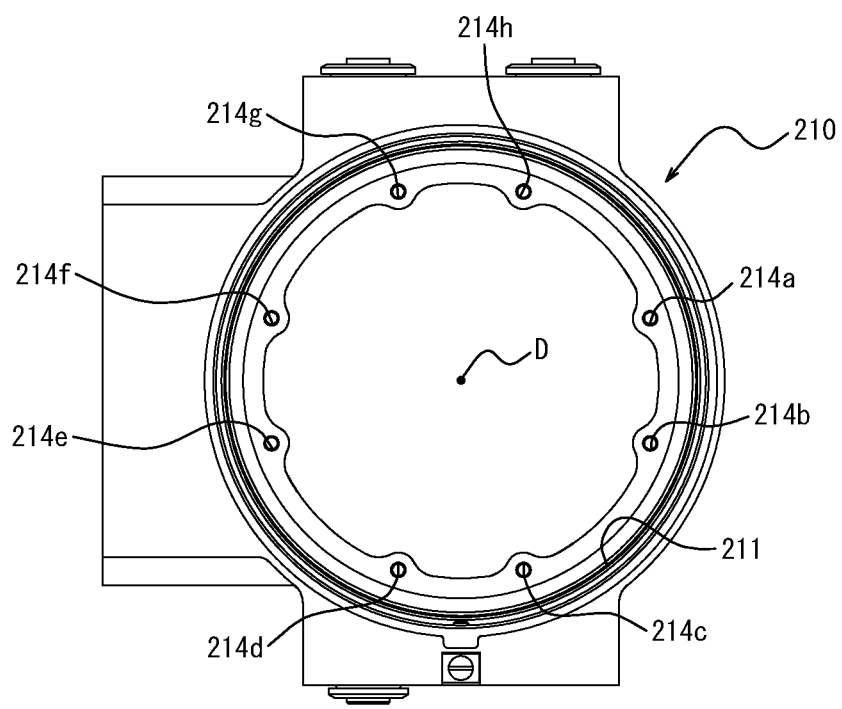
FIG. 8 illustrates an example of a fourth connecting portion of a casing.

The form of connection between the circuit portion 220 and the casing 210 is described below with reference to FIGS. 7 and 8. The circuit portion 220 includes a third connecting portion, details of which are provided below. The casing 210 includes a fourth connecting portion. One of the third connecting portion and the fourth connecting portion includes a plurality of third connecting elements arranged about the display axis D. The other one of the third connecting portion and the fourth connecting portion includes one or more fourth connecting elements connectable to the third connecting elements at a plurality of rotation positions where the display 221 is fixable relative to the sensor probe 100 about the display axis D. FIG. 7 illustrates an example of the third connecting portion of the circuit portion 220. FIG. 8 illustrates an example of the fourth connecting portion of the casing 210. The circuit portion 220 and the casing 210 mechanically connect to each other via the third connecting portion of the circuit portion 220 and the fourth connecting portion of the casing 210.

In the example illustrated in FIG. 7, the circuit portion 220 includes four third holes 222a to 222d as the third connecting portion at the back end illustrated in FIG. 4. In the example illustrated in FIG. 8, the casing 210 includes eight fourth holes 214a to 214h as the fourth connecting portion on the inside of the opening 211.

The four third holes 222a to 222d can be arranged simultaneously at positions corresponding to the four fourth holes 214a, 214b, 214e, and 214f among the eight fourth holes 214a to 214h. In this state, screws or the like can be attached so as to pass through the four third holes 222a to 222d and the four fourth holes 214a, 214b, 214e, and 214f to connect the circuit portion 220 and the casing 210 physically. The casing 210 and the circuit portion 220, for example, are electrically connected via cables which is not illustrated in the figures. The casing 210 and the circuit portion 220, for example, comprise the same configuration as the first connector and the second connector and can be mechanically and electrically connected in the same way as the mechanical and electrical connection of the sensor probe 100 and the circuit housing 200. In greater detail, the third hole 222a can be arranged at a position corresponding to the fourth hole 214f, the third hole 222b at a position corresponding to the fourth hole 214e, the third hole 222c at a position corresponding to the fourth hole 214b, and the third hole 222d at a position corresponding to the fourth hole 214a (first arrangement position). The third hole 222a can also be arranged at a position corresponding to the fourth hole 214b, the third hole 222b at a position corresponding to the fourth hole 214a, the third hole 222c at a position corresponding to the fourth hole 214f, and the third hole 222d at a position corresponding to the fourth hole 214e (second arrangement position). In the state in which the circuit portion 220 is connected to the casing 210 at the second arrangement position, the circuit portion 220 is at a rotation position rotated substantially 180° about the display axis D relative to the casing 210 from the state in which the circuit portion 220 is connected to the casing 210 at the first arrangement position.

The four third holes 222a to 222d can also be arranged simultaneously at positions corresponding to the four fourth holes 214c, 214d, 214g, and 214h among the eight fourth holes 214a to 214h. In this state, screws or the like can be attached so as to pass through the four third holes 222a to 222d and the four fourth holes 214c, 214d, 214g, and 214h to connect the circuit portion 220 and the casing 210 physically. In greater detail, the third hole 222a can be arranged at a position corresponding to the fourth hole 214h, the third hole 222b at a position corresponding to the fourth hole 214g, the third hole 222c at a position corresponding to the fourth hole 214d, and the third hole 222d at a position corresponding to the fourth hole 214c (third arrangement position). The third hole 222a can also be arranged at a position corresponding to the fourth hole 214d, the third hole 222b at a position corresponding to the fourth hole 214c, the third hole 222c at a position corresponding to the fourth hole 214h, and the third hole 222d at a position corresponding to the fourth hole 214g (fourth arrangement position). In the state in which the circuit portion 220 is connected to the casing 210 at the fourth arrangement position, the circuit portion 220 is at a rotation position rotated substantially 180° about the display axis D relative to the casing 210 from the state in which the circuit portion 220 is connected to the casing 210 at the third arrangement position. In the state in which the circuit portion 220 is connected to the casing 210 at the third arrangement position, the circuit portion 220 is at a rotation position rotated substantially 90° clockwise about the display axis D relative to the casing 210 from the state in which the circuit portion 220 is connected to the casing 210 at the first arrangement position.

The eight fourth holes 214a to 214h serving as the fourth connecting portion in the example illustrated in FIGS. 7 and 8 thus include the four fourth holes 214b, 214d, 214f, and 214h as the above-described plurality of third connecting elements. At this time, the four third holes 222a to 222d serving as the third connecting portion include the two third holes 222a and 222c as the above-described one or more fourth connecting elements. The eight fourth holes 214a to 214h serving as the fourth connecting portion also include the four fourth holes 214a, 214c, 214e, and 214g as the above-described plurality of third connecting elements. At this time, the four third holes 222a to 222d serving as the third connecting portion include the two third holes 222b and 222d as the above-described one or more fourth connecting elements.

The circuit portion 220 is thus fixable at a plurality of rotation positions relative to the casing 210 about the display axis D. The circuit portion 220 includes the display 221, and the rotation position of the sensor probe 100 about the display axis D relative to the casing 210 is fixed. Accordingly, the display 221 is fixable at a plurality of rotation positions relative to the sensor probe 100 about the display axis D. In the present embodiment, the plurality of rotation positions of the display 221 relative to the sensor probe 100 include four rotation positions differing by substantially 90°.

FIGS. 7 and 8 illustrate the four third holes 222a to 222d serving as the third connecting portion and the eight fourth holes 214a to 214h serving as the fourth connecting portion, but as long as a plurality of at least one of the third connecting portion and the fourth connecting portion is provided, the number thereof is not limited. Any plural number of arrangement positions at which the third connecting portion can be arranged in correspondence with the fourth connecting portion may be provided, such as two, three, or five or more. The plurality of rotation positions of the display 221 relative to the sensor probe 100 may correspondingly be two, three, or five or more.

Instead of or in addition to the circuit portion 220 being fixable at a plurality of rotation positions about the display axis D relative to the casing 210, the display 221 may be fixable at a plurality of rotation positions about the display axis D relative to another portion of the circuit portion 220. In this case, the display 221 and the other portion of the circuit portion 220 may be connectable in the same way as the above-described connection via the first connecting portion of the sensor probe 100 and the second connecting portion of the circuit housing 200. In other words, the display 221 may include the third connecting portion, and another portion of the circuit portion 220 may include the fourth connecting portion. One of the third connecting portion and the fourth connecting portion may include a plurality of third connecting elements arranged about the display axis D. The other one of the third connecting portion and the fourth connecting portion may include one or more fourth connecting elements connectable to the third connecting elements at a plurality of rotation positions where the display 221 is fixable relative to the sensor probe 100 about the display axis D.

Figure 9:
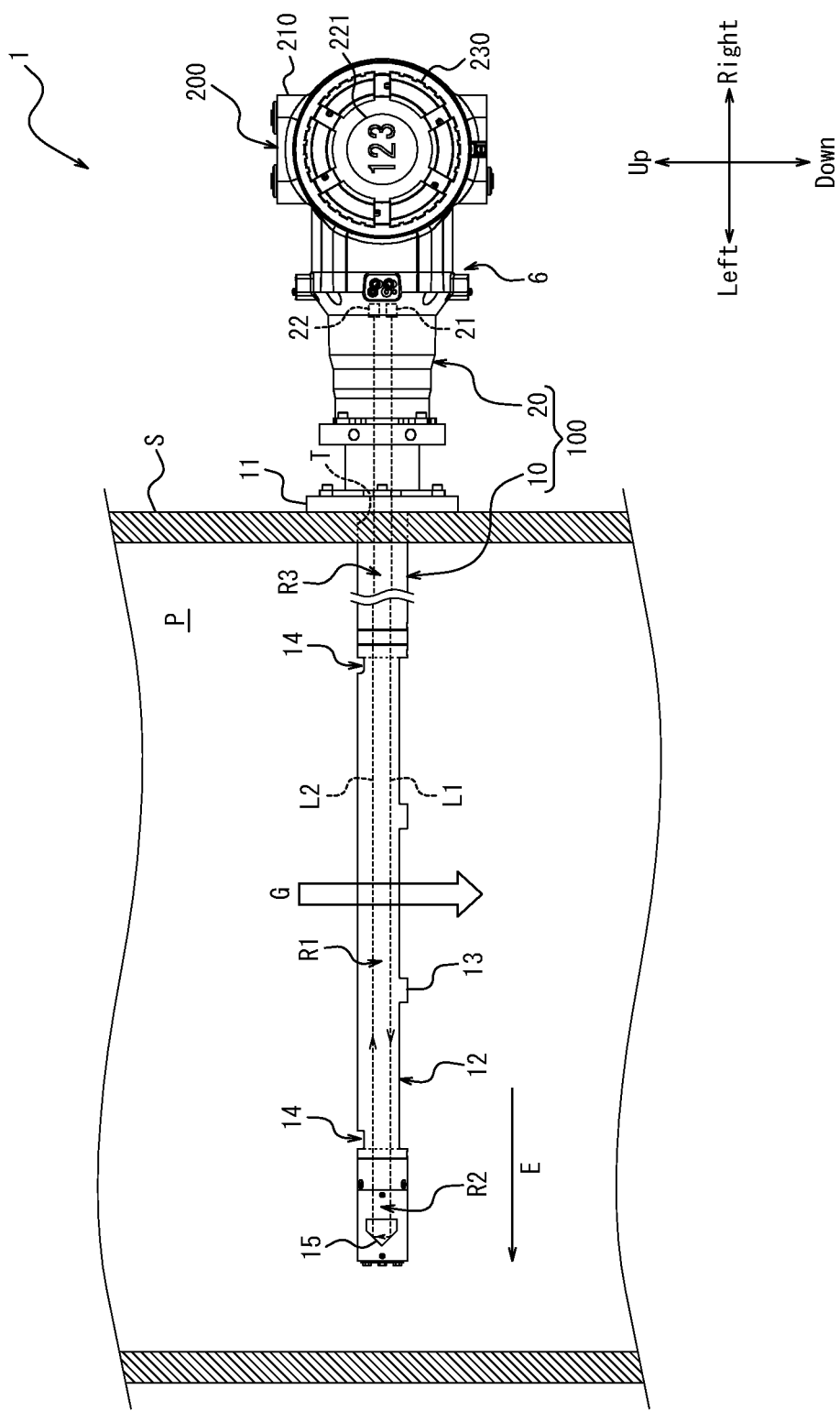
FIG. 9 is a front view illustrating a second usage state of the measurement apparatus of FIG. 1.

FIG. 9 illustrates a second usage state of the gas analyzer 1 according to the present embodiment. With respect to the gas analyzer 1 in the first usage state illustrated in FIG. 3, the sensor probe 100 of the gas analyzer 1 in the present usage state is rotated substantially 180° relative to the circuit housing 200 about the connection axis B (see FIG. 4 and the like). In the example in FIG. 9, the flow direction of the gas to be measured G is the direction from top to bottom, i.e. opposite from the example illustrated in FIG. 3. With respect to this flow direction of the gas to be measured G, the probe 10 is required to be used with the notches 14 facing upward, i.e. upstream in the flow direction, and the opening 12 facing downward, i.e. downstream in the flow direction, as illustrated in FIG. 9. When the probe 10 is used while having the aforementioned orientation relative to the flow direction of the gas to be measured G, the measurement region R1 can be filled with the gas to be measured G, while the regions R2 and R3 can be filled with a purge gas, as described above.

Furthermore, as illustrated in FIG. 9, the rotation position of the display 221 about the display axis D (see FIG. 4 and the like) relative to the sensor probe 100 of the gas analyzer 1 in the present usage state is the same as in the gas analyzer 1 in the first usage state illustrated in FIG. 3. The display direction C of the display 221 in the example illustrated in FIG. 9 is a direction facing out of the page. The display content is displayed in the left-right direction for better visibility for a user standing upright, so that the angle of the content displayed by the display 221 is set to the angle desired by the user.

Figure 10:
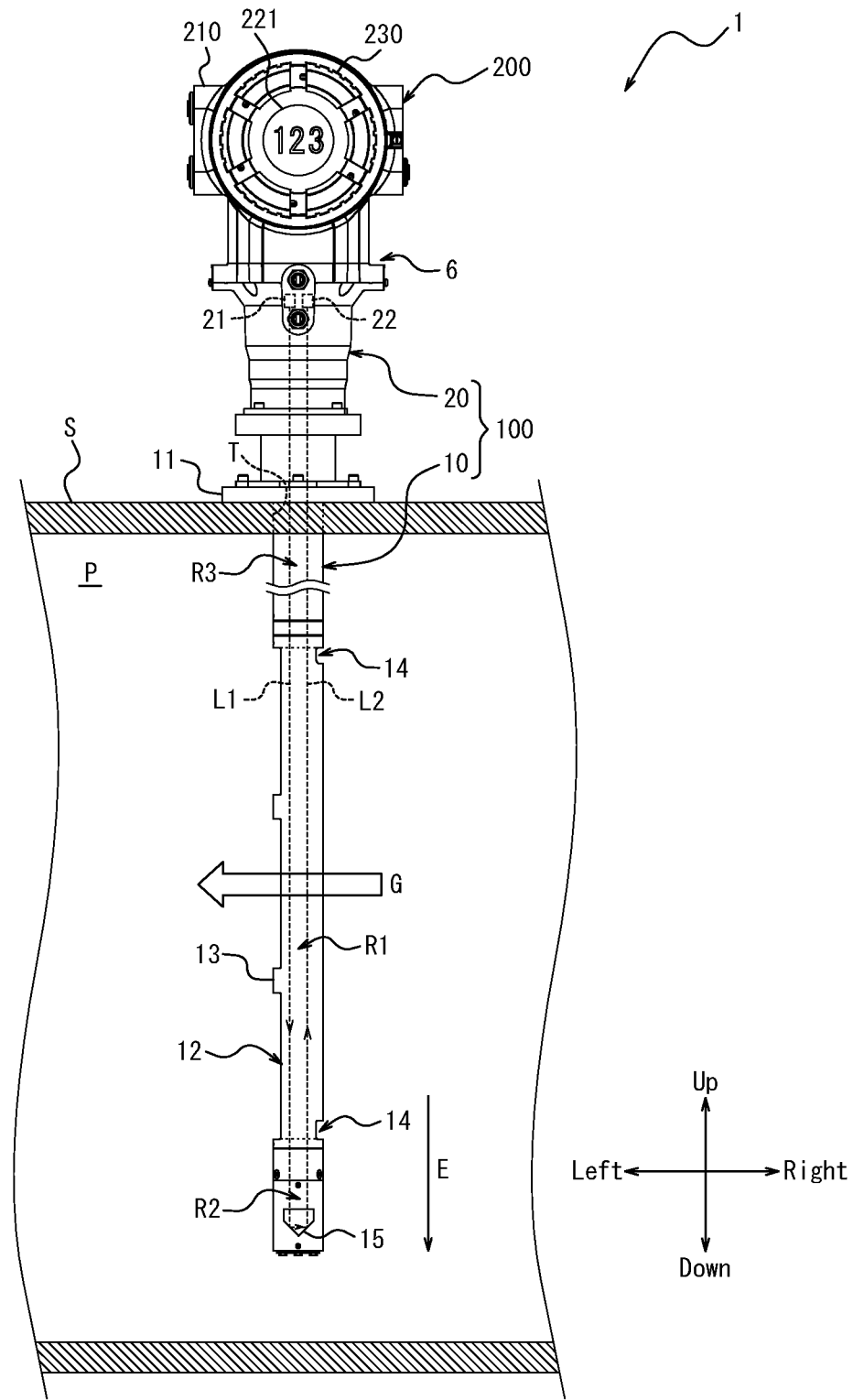
FIG. 10 is a front view illustrating a third usage state of the measurement apparatus of FIG. 1.

FIG. 10 illustrates a third usage state of the gas analyzer 1 according to the present embodiment. In the example in FIG. 10, the flow path P extends in the left-right direction, and the flow direction of the gas to be measured G is the direction from right to left. Accordingly, the gas analyzer 1 in the present usage state is used by rotating the gas analyzer 1 in the usage state illustrated in FIG. 3 counterclockwise 90° about an axis orthogonal to the page. Consequently, as illustrated in FIG. 10, the probe 10 is used with the notches 14 facing to the right, i.e. upstream in the flow direction, and the opening 12 facing to the left, i.e. downstream in the flow direction. The measurement region R1 can therefore be filled with the gas to be measured G, while the regions R2 and R3 are filled with a purge gas, as described above.

With respect to the gas analyzer 1 in the first usage state illustrated in FIG. 3, the display 221 of the gas analyzer 1 in the present usage state is rotated 90° clockwise about the display axis D (see FIG. 4 and the like) relative to the sensor probe 100, as illustrated in FIG. 10. The display direction C of the display 221 thus becomes a direction facing out of the page, as illustrated in FIG. 10, and the display content is displayed in the left-right direction for better visibility for a user standing upright, so that the angle of the content displayed by the display 221 is set to the angle desired by the user.

Figure 11:
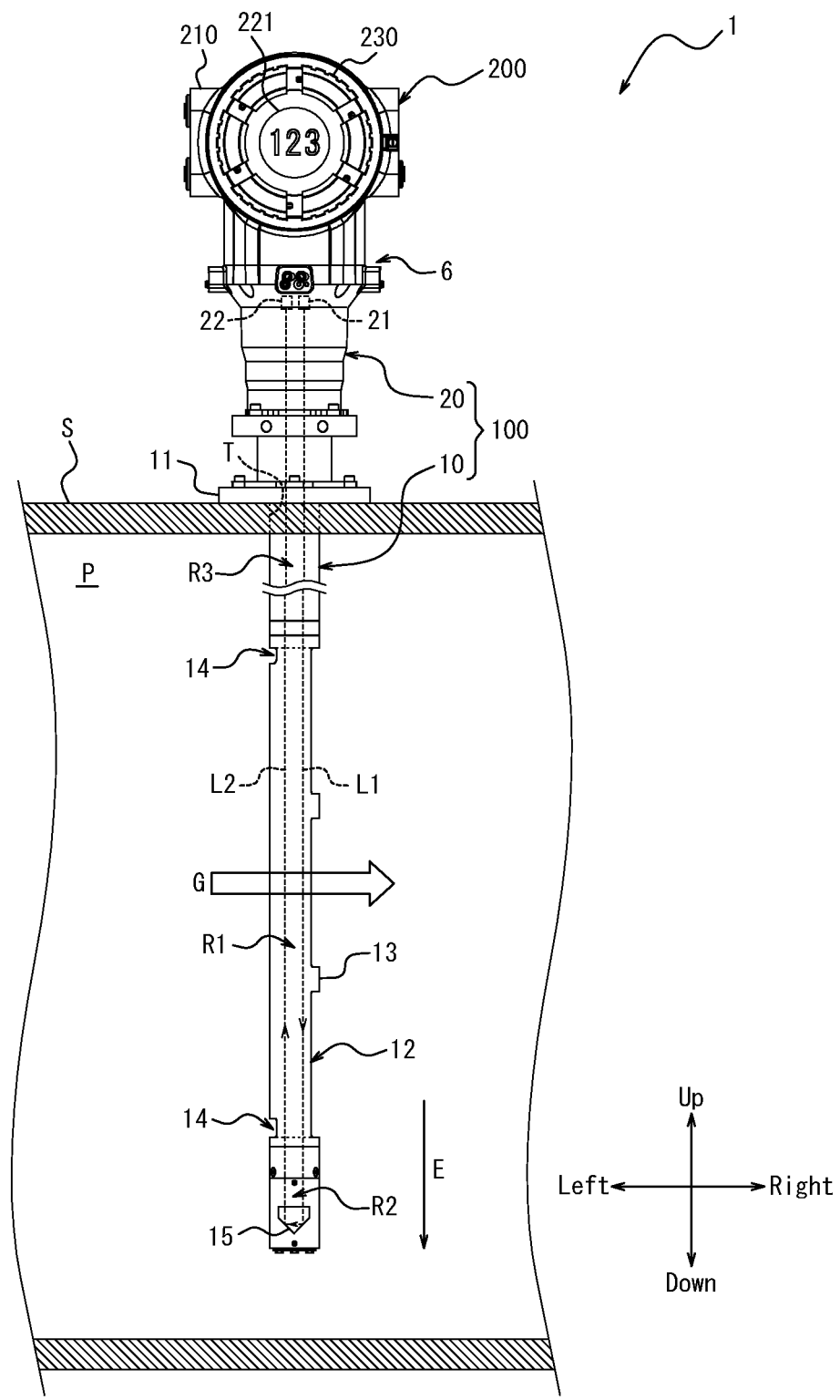
FIG. 11 is a front view illustrating a fourth usage state of the measurement apparatus of FIG. 1.

FIG. 11 illustrates a fourth usage state of the gas analyzer 1 according to the present embodiment. In the example in FIG. 11, the flow path P extends in the left-right direction, and the flow direction of the gas to be measured G is the direction from left to right. Accordingly, the gas analyzer 1 in the present usage state is used by rotating the gas analyzer 1 in the usage state illustrated in FIG. 9 counterclockwise 90° about an axis orthogonal to the page. Consequently, as illustrated in FIG. 11, the probe 10 is used with the notches 14 facing to the left, i.e. upstream in the flow direction, and the opening 12 facing to the right, i.e. downstream in the flow direction. The measurement region R1 can therefore be filled with the gas to be measured G, while the regions R2 and R3 are filled with a purge gas, as described above.

With respect to the gas analyzer 1 in the second usage state illustrated in FIG. 9, the display 221 of the gas analyzer 1 in the present usage state is rotated 90° clockwise about the display axis D (see FIG. 4 and the like) relative to the sensor probe 100, as illustrated in FIG. 11. The display direction C of the display 221 thus becomes a direction facing out of the page, as illustrated in FIG. 11, and the display content is displayed in the left-right direction for better visibility for a user standing upright, so that the angle of the content displayed by the display 221 is set to the angle desired by the user.

The gas analyzer 1 serving as a measurement apparatus according to the present embodiment includes a sensor probe 100 and a circuit housing 200, as described above. The sensor probe 100 is insertable through an opening provided in the flow path wall S of the flow path P through which the gas to be measured G, which is a fluid to be measured, flows. The sensor probe 100 is used in a predetermined orientation relative to the flow direction of the gas to be measured G. The circuit housing 200 includes the display 221 disposed outside of the flow path P and is connected to the sensor probe 100. The circuit housing 200 is fixable at a plurality of rotation positions relative to the sensor probe 100 about an axis (connection axis B) along the insertion direction E of the sensor probe 100. Accordingly, the gas analyzer 1 serving as a measurement apparatus according to the present embodiment allows the display direction C of the display 221 to be selected without regard for the orientation of the sensor probe 100.

The display 221 in the gas analyzer 1 serving as a measurement apparatus according to the present embodiment is fixable at a plurality of rotation positions relative to the sensor probe 100 about an axis (display axis D) along the display direction C, as described above. Accordingly, the gas analyzer 1 serving as a measurement apparatus according to the present embodiment allows the angle of the content displayed by the display 221 to be selected without regard for the orientation of the sensor probe 100.

The rotation positions that the circuit housing 200 can adopt relative to the sensor probe 100 in the gas analyzer 1 serving as a measurement apparatus according to the present embodiment include four rotation positions differing by substantially 90°, as described above. Here, when the flow path P is piping, a flue, a combustion furnace, or the like, the flow path P typically extends in the horizontal or vertical direction. Accordingly, if the circuit housing 200 is fixed relative to the sensor probe 100 at four rotation positions differing by substantially 90°, the display direction C of the display 221 can easily be oriented in the direction desired by the user.

The rotation positions that the display 221 can adopt relative to the sensor probe 100 in the gas analyzer 1 serving as a measurement apparatus according to the present embodiment include four rotation positions differing by substantially 90°, as described above. Here, when the flow path P is piping, a flue, a combustion furnace, or the like, the flow path P typically extends in the horizontal or vertical direction. Accordingly, if the display 221 is fixed relative to the sensor probe 100 at four rotation positions differing by substantially 90°, the angle of the content displayed by the display 221 can easily be set to the angle desired by the user.

The insertion direction E of the sensor probe 100 in the gas analyzer 1 serving as a measurement apparatus according to the present embodiment is a direction substantially orthogonal to the extending direction of the flow path P, and the display direction C of the display 221 is a direction substantially orthogonal to the insertion direction E of the sensor probe 100, as described above. Here, when the flow path P is piping, a flue, a combustion furnace, or the like, the flow path P typically extends in the horizontal or vertical direction. Providing the insertion direction E and the display direction C with the aforementioned relationship relative to the extending direction of the flow path P thus makes it even easier to orient the display direction C of the display 221 in the direction desired by the user.

The sensor probe 100 in the gas analyzer 1 serving as a measurement apparatus according to the present embodiment includes the attachment portion 11 attachable to the outer surface of the flow wall S, as described above. The attachment portion 11 is positioned towards the flow path P from the connection position 6 between the sensor probe 100 and the circuit housing 200. Accordingly, the rotation position of the circuit housing 200 relative to the sensor probe 100 about the connection axis B can be changed even after the sensor probe 100 is installed in the flow path P.

The gas analyzer 1 has been described above as an example of a measurement apparatus according to the present embodiment. The measurement apparatus according to the present embodiment is not, however, limited to the gas analyzer 1. For example, the measurement apparatus may be a Karman vortex flow meter that includes the below-described sensor probe, instead of the sensor probe 100, and a circuit housing similar to the circuit housing 200. The circuit housing is fixable at a plurality of rotation positions relative to the sensor probe about an axis along the insertion direction of the sensor probe into the flow path. The sensor probe provided in the Karman vortex flow meter includes a vortex shedder disposed in the flow path through which the fluid to be measured flows and a sensor for detecting fluid vortices generated by the vortex shedder. The flow of the fluid to be measured can be measured by analysis, within the circuit housing, of information on the vortices detected by the sensor. The sensor probe is used in a predetermined orientation relative to the flow direction of the fluid to be measured so that the long sides of the vortex shedder are positioned upstream in the flow path.

The present disclosure is not limited to the configurations specified in the above embodiments, and a variety of modifications may be made without departing from the scope of the claims.

INDUSTRIAL APPLICABILITY

The present disclosure relates to a measurement apparatus.

The invention claimed is:

1. A measurement apparatus comprising:
a sensor probe insertable through an opening provided in a flow path wall of a flow path through which a fluid to be measured flows, the sensor probe being used in a predetermined orientation relative to a flow direction of the fluid to be measured; and
a circuit housing that comprises a display and connects to the sensor probe, the display being disposed outside of the flow path;
wherein the circuit housing is fixable at a plurality of rotation positions relative to the sensor probe about an axis along an insertion direction of the sensor probe, and
wherein the sensor probe comprises a first connecting portion;
wherein the circuit housing comprises a second connecting portion that connects to the first connecting portion; and
wherein one of the first connecting portion and the second connecting portion comprises a plurality of first connecting elements arranged about the axis along the insertion direction, and another one of the first connecting portion and the second connecting portion comprises one or more second connecting elements connectable to the plurality of first connecting elements at the plurality of rotation positions.

2. The measurement apparatus of claim 1, wherein the display is fixable at a plurality of rotation positions relative to the sensor probe about an axis along a display direction.

3. The measurement apparatus of claim 2,
wherein the circuit housing comprises a casing and a circuit portion that comprises the display;
wherein the circuit portion comprises a third connecting portion;
wherein the casing comprises a fourth connecting portion; and
wherein one of the third connecting portion and the fourth connecting portion comprises a plurality of third connecting elements arranged about the axis along the display direction, and another one of the third connecting portion and the fourth connecting portion comprises one or more fourth connecting elements connectable to the plurality of third connecting elements at the plurality of rotation positions where the display is fixable relative to the sensor probe about the axis along the display direction.

4. The measurement apparatus of claim 2,
wherein the circuit housing comprises a circuit portion that comprises the display;
wherein the display comprises a third connecting portion;
wherein a portion of the circuit portion other than the display comprises a fourth connecting portion; and
wherein one of the third connecting portion and the fourth connecting portion comprises a plurality of third connecting elements arranged about the axis along the display direction, and another one of the third connecting portion and the fourth connecting portion comprises one or more fourth connecting elements connectable to the plurality of third connecting elements at the plurality of rotation positions where the display is fixable relative to the sensor probe about the axis along the display direction.

5. The measurement apparatus of claim 2, wherein the plurality of rotation positions of the circuit housing relative to the sensor probe includes four rotation positions differing by substantially 90°.

6. The measurement apparatus of claim 5, wherein the plurality of rotation positions of the display relative to the sensor probe includes four rotation positions differing by substantially 90°.

7. The measurement apparatus of claim 6,
wherein the insertion direction is a direction substantially orthogonal to an extending direction of the flow path; and
wherein the display direction is a direction substantially orthogonal to the insertion direction.

8. The measurement apparatus of claim 1,
wherein the sensor probe comprises an attachment portion attachable to an outer surface of the flow path wall; and
wherein the attachment portion is positioned towards the flow path from a connection position between the sensor probe and the circuit housing.

9. The measurement apparatus of claim 1, wherein each of the plurality of first connecting elements and the one or more second connecting elements is a connector configured to mechanically and electrically connect the sensor probe and the circuit housing to each other.

10. The measurement apparatus of claim 9, wherein the connector is a floating connector.

11. A measurement apparatus comprising:
a sensor probe insertable through an opening provided in a flow path wall of a flow path through which a fluid to be measured flows, the sensor probe being used in a predetermined orientation relative to a flow direction of the fluid to be measured; and
a circuit housing that comprises a display and connects to the sensor probe, the display being disposed outside of the flow path;
wherein the circuit housing is fixable at a plurality of rotation positions relative to the sensor probe about an axis along an insertion direction of the sensor probe,
wherein the sensor probe comprises:
an optical emitter configured to irradiate measurement light into a measurement region including the fluid to be measured;
a probe extending along an optical axis of the measurement light so as to overlap the measurement region;

a reflector positioned at an opposite tip of the probe from the optical emitter and configured to reflect the measurement light; and an optical receiver configured to receive the measurement light reflected by the reflector.

\* \* \* \* \*